(12) United States Patent
Lee et al.

(10) Patent No.: US 7,728,172 B2
(45) Date of Patent: Jun. 1, 2010

(54) PRECURSOR, THIN LAYER PREPARED INCLUDING THE PRECURSOR, METHOD OF PREPARING THE THIN LAYER AND PHASE-CHANGE MEMORY DEVICE

(75) Inventors: Jung-Hyun Lee, Yongin-si (KR); Yoon-Ho Khang, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 12/078,751

(22) Filed: Apr. 4, 2008

(65) Prior Publication Data

US 2008/0258127 A1 Oct. 23, 2008

Related U.S. Application Data

(63) Continuation of application No. 11/349,135, filed on Feb. 8, 2006, now Pat. No. 7,371,429.

(30) Foreign Application Priority Data

Feb. 14, 2005 (KR) .................. 10-2005-0012037

(51) Int. Cl.
  *C07C 395/00* (2006.01)
  *C23C 16/00* (2006.01)
(52) U.S. Cl. .............. 562/899; 427/255.28; 257/40
(58) Field of Classification Search ........... 562/899; 427/255.28; 257/40
  See application file for complete search history.

(56) References Cited

U.S. PATENT DOCUMENTS

| 6,752,869 B2 | 6/2004 | Lee et al. |
| 2003/0185981 A1 | 10/2003 | Min et al. |
| 2006/0049447 A1 | 3/2006 | Lee et al. |
| 2006/0138393 A1 | 6/2006 | Seo et al. |

FOREIGN PATENT DOCUMENTS

| EP | 1067595 | 1/2001 |
| KR | 2002-0084616 | 11/2002 |
| KR | 10-2003-0058595 | 7/2003 |
| KR | 1020040076225 | 8/2004 |
| KR | 10-2004-0100499 | 12/2004 |

OTHER PUBLICATIONS

Korean Office Action dated Jul. 20, 2006 with English translation.
Bunton et al., IEEE Transaction on Electron Devices, vol. ED-20, No. 2, pp. 140-144 (1973).
Liu et al., Semiconductor Science and Technology, vol. 19, pp. L61-L64 (2004).
Björgvinsson et al., Inorganic Chemistry, vol. 29, No. 26, pp. 5140-5143 (1990).

*Primary Examiner*—Porfirio Nazario Gonzalez
(74) *Attorney, Agent, or Firm*—Harness, Dickey & Pierce, P.L.C.

(57) ABSTRACT

A Te precursor containing Te, a 15-group compound (for example, N) and/or a 14-group compound (for example, Si), a method of preparing the Te precursor, a Te-containing chalcogenide thin layer including the Te precursor, a method of preparing the thin layer; and a phase-change memory device. The Te precursor may be deposited at lower temperatures for forming a Te-containing chalcogenide thin layer doped with a 15-group compound (for example, N) and/or a 14-group compound (for example, Si). For example, the Te precursor may employ plasma enhanced chemical vapor deposition (PECVD) or plasma enhanced atomic layer deposition (PEALD) at lower deposition temperatures. The GST phase-change layer doped with a 15-group compound (for example, N) and/or a 14-group compound (for example, Si) formed by employing the Te precursor may have a decreased reset current, and thus when a memory device including the same is employed, its integration may be possible, and operation with higher capacity and/or higher speed may be possible.

1 Claim, 6 Drawing Sheets

US 7,728,172 B2

PRECURSOR, THIN LAYER PREPARED INCLUDING THE PRECURSOR, METHOD OF PREPARING THE THIN LAYER AND PHASE-CHANGE MEMORY DEVICE

PRIORITY STATEMENT

This application is a continuation application of and claims priority under 35 U.S.C. 120/121 to U.S. application Ser. No. 11/349,135, filed Feb. 8, 2006 now U.S. Pat. No. 7,371,429, the disclosure of which is incorporated herein in its entirety by reference, and claims the benefit of Korean Patent Application No. 10-2005-0012037, filed on Feb. 14, 2005, in the Korean Intellectual Property Office, the disclosure of which is incorporated herein in its entirety by reference.

BACKGROUND OF THE INVENTION

1. Field of the Invention

Example embodiments of the present invention relate to a precursor, for example, a Te precursor, for lower temperature deposition, a thin layer, for example, a Te-containing chalcogenide thin layer, prepared by employing the precursor; and a method of preparing the thin layer, and for example, to a precursor for lower temperature deposition containing Te, a 15-group compound and/or a 14-group compound; a chalcogenide thin layer doped with a 15-group compound and/or a 14-group compound and prepared at lower temperature by employing the precursor, and a method of preparing the thin layer. Also, example embodiments of the present invention relate to a phase-change memory device including a phase-change layer formed by employing the precursor.

2. Description of the Related Art

A phase-change material is a material that may have a crystalline state or an amorphous state, depending on temperature. The crystalline state has lower resistance than the amorphous state and has an ordered regular atomic arrangement. The crystalline state and the amorphous state may be reversible. That is, the crystalline state may be changed to the amorphous state and the amorphous state may be changed back into the crystalline state. A phase-change random access memory device (PRAM) is a memory device applying the characteristics that a phase-change material has reversible states and distinguishable resistances.

The general form of a PRAM may include a phase-change layer electrically connected to a source or a drain area of a transistor through a contact plug. Operation as a memory may be performed by employing the difference in resistance due to the change of crystal structure in the phase-change layer. FIG. 1 shows the general form of PRAM according to the conventional art. Hereinafter, referring to FIG. 1, the general structure of a conventional PRAM is described.

Referring to FIG. 1, on the transistor substrate 10, a first impurity area 11a and a second impurity area 11b may be formed, and a gate insulating layer 12 and a gate electrode layer 13 may be formed in contact with the two impurity areas. The first impurity area 11a may be referred to a source and the second impurity area 11b may be referred to a drain.

On the first impurity area 11a, the gate electrode layer 13 and on the second impurity area 11b, the insulating layer 15 may be formed, and a contact plug 14 may be formed in contact with the second impurity area 11b, penetrating the insulating layer 15. On the contact plug 14, a lower electrode 16 may be formed, and on the lower electrode 16, the phase-change layer 17 and the upper electrode 18 may be formed.

A technique of storing data in the PRAM having the structure described above may be as follows. Joule heat is generated at the contact area of the lower electrode 16 and the phase-change layer 17 by the electric current applied through the second impurity area 11b and the lower electrode 16. Data is stored by changing the crystal structure of the phase-change layer 17 with the Joule heat. That is, the crystal structure of the phase-change layer 17 is changed into a crystalline state or an amorphous state by changing an applied electric current. Accordingly, the previous data stored can be distinguished since the resistance is changed in response to the change between the crystalline state and the amorphous state.

Various types of phase-change material that can be applied to memory devices are known, and a representative example thereof is GST (GeSbTe) based alloy. Transistor memory devices including various types of chalcogenide material layers are known.

It may be beneficial to decrease a consumed electric current value in order to improve the performance of a memory device. For a PRAM that includes a GST layer, a phase-change material being used frequently, the reset current value, e.g., the current value for transition from crystalline state to amorphous state is high.

FIG. 2 is a graph showing heating temperatures for the Reset/Set Programming of a memory device that uses GST ($Ge_2Sb_2Te_5$) in a phase-change layer.

Referring to FIG. 2, it may be seen that crystallization can be achieved by keeping the temperature lower than the melting point for a period of time, for set programming for GST, e.g., changing the amorphous state into the crystalline state. It may be seen that temperature should be elevated to almost the melting point (Tm) and then cooled, for reset programming, e.g., changing the crystalline state into the amorphous state. The current needed to elevate the temperature to the melting point (Tm) is relatively high. As a result, there may be a limit in realizing higher integrated memory devices.

SUMMARY

Example embodiments of the present invention provide a precursor, for example, a Te precursor, that may be deposited at lower temperatures, a thin layer, for example, a Te-containing chalcogenide thin layer, for example, a GST thin layer, employing the precursor that consumes less current for reset/set programming, a method of preparing the thin layer by employing the precursor, and/or a phase-change memory device including a phase-change layer, for example, a phase-change layer formed by employing the precursor.

According to an example embodiment of the present invention, there is provided a Te precursor including Te, a 15-group compound and/or a 14-group compound.

According to an example embodiment of the present invention, there is provided a Te precursor containing Te, N and/or Si.

More generally, the precursor according to example embodiments of the present invention may be defined as one or more 16-group compounds (for example, Te) in combination with one or more 15-group compounds (for example, N) or one or more 14-group compounds (for example, Si) or both.

According to another example embodiment of the present invention, there is provided a thin layer, for example, a Te-containing chalcogenide thin layer, prepared by employing a Te precursor including Te, a 15-group compound (for example, N) and/or a 14-group compound (for example, Si).

According to another example embodiment of the present invention, there is provided a method of preparing a thin layer, for example, a Te-containing chalcogenide thin layer, comprising depositing one or more of the precursor(s) described above at deposition temperatures below 350° C.

According to another example embodiment of the present invention, there is provided a phase-change memory device including a transistor substrate, including a first impurity area and a second impurity area formed on the transistor substrate, a gate structure formed on a channel area between the first impurity area and the second impurity area, a lower electrode connected to the second impurity area, a phase-change layer, for example, a GST phase-change layer formed on the lower electrode, and an upper electrode formed on the phase-change layer, wherein the phase-change layer is formed by employing a Ge precursor, a Sb precursor and a Te precursor including Te, a 15-group compound (for example, N) and/or a 14-group compound (for example, Si).

By employing a precursor according to example embodiments of the present invention, a thin layer having more uniform thickness, suitable for various devices may be obtained by lower temperature deposition. For example, a thin layer, for example, a GST thin layer, obtained by employing a Te precursor may be doped with a 15-group compound (for example, N) and/or a 14-group compound (for example, Si), and thus the reset current that may be applied to change the crystal structure may be decreased. Accordingly, a phase-change memory device with higher performance may be realized.

BRIEF DESCRIPTION OF THE DRAWINGS

The above and other features and advantages of example embodiments of the present invention will become more apparent by describing in detail example embodiments thereof with reference to the attached drawings in which.

DETAILED DESCRIPTION OF EXAMPLE EMBODIMENTS OF THE INVENTION

Figure 1:
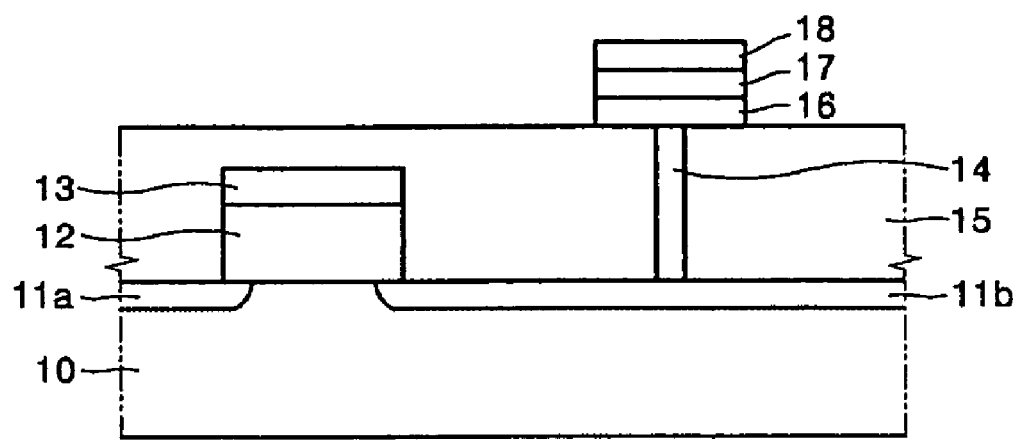
FIG. 1 is a schematic cross-sectional view in the general form of PRAM according to the conventional art.
Figure 2:
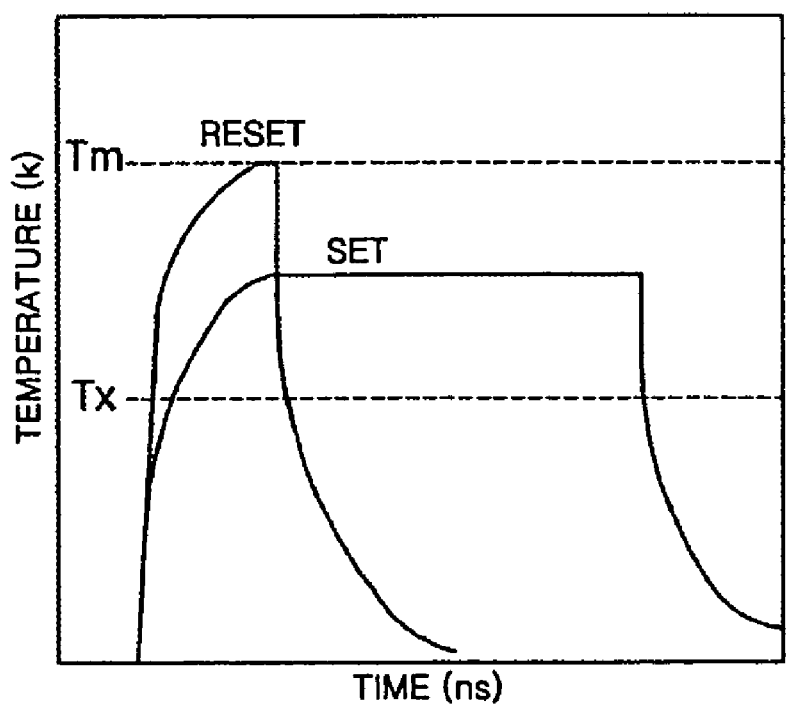
FIG. 2 is a graph showing heating temperatures for the Reset/Set Programming of a memory device including a phase-change layer made of $Ge_2Sb_2Te_5$.

Example embodiments of the present invention will now be described more fully hereinafter with reference to the accompanying drawings, in which example embodiments of the invention are shown. This invention may, however, be embodied in many different forms and should not be construed as being limited to the example embodiments set forth herein. Rather, these example embodiments are provided so that this disclosure will be thorough and complete, and will fully convey the scope of the invention to those skilled in the art. Like numbers refer to like elements throughout the specification.

The Te precursor for lower temperature deposition according to example embodiments of the present invention may contain Te, a 15-group compound (for example, N) and/or a 14-group compound (for example, Si). Herein, the term "for lower temperature deposition" relating to the Te precursor is intended to indicate that, for the Te precursor according to example embodiments of the present invention, the depositing temperature for a deposition process for forming a thin layer having desired thickness is relatively low over the conventional Te precursor, for example, not containing a 15-group compound (for example, N) and/or a 14-group compound (for example, Si). The term "lower temperature" refers to, for example, temperatures below about 350° C., and will be described in more detail hereinafter.

For example, the Te precursor for lower temperature deposition according to example embodiments of the present invention may be represented by formula I below:

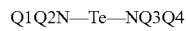

$$Q1Q2N\text{—}Te\text{—}NQ3Q4 \qquad \text{I}$$

wherein Q1, Q2, Q3 and Q4 are each independently a hydrogen atom, a linear or branched C1-30 alkyl group, or SiR1R2R3, in which the R1, R2 and R3 are each independently hydrogen atom, or a linear or branched C1-30 alkyl group, and at least one of the Q1, Q2, Q3 and Q4 are SiR1R2R3.

The Te precursor represented by the formula I contains a 15-group compound (for example, N) and/or a 14-group compound (for example, Si). Accordingly, when a Te-containing thin layer employing the Te precursor is formed, another a 15-group compound (for example, N) source and/or a 14-group compound (for example, Si) source is not required for doping. Further, when the Te precursor having the formula I is employed, a Te-containing chalcogenide thin layer, for example, GST thin layer, having the performance (e.g., durability, electrical property, etc) suitable for being used in various transistor devices at lower deposition temperatures, for example, below 350° C., or for example, 200° C. to 350° C. can be formed.

In the formula I, at least one of the Q1, Q2, Q3 and Q4 may be SiR1R2R3 so that the Te precursor according to example embodiments of the present invention may contain a 14-group compound (for example, Si).

For example, in the formula I, R1, R2 and R3 may be each independently, but are not limited to, a hydrogen atom, a methyl group, an ethyl group, an isopropyl group, a butyl group, a pentyl group and/or a hexyl group.

A Te precursor according to example embodiments of the present invention may be represented by formula II below:

$$Te[NH(Si(CH_3)_3)]_2 \qquad \text{II}$$

As is clear from the above, more generally, the precursor according to example embodiments of the present invention may be defined as one or more 16-group compounds (for example, Te) in combination with one or more 15-group compounds (for example, N) or one or more 14-group compounds (for example, Si) or both.

In preparing the Te precursor for lower temperature deposition, any of the various known methods may be employed.

Among the known methods, a method of preparing the Te precursor according to example embodiments of the present invention is described as follows.

An aminosilane-based compound having N—Si bonds may be reacted with an alkali metal-containing material to prepare an aminosilane-based compound substituted with at least one alkali metal. The aminosilane-based compounds may include, but are not limited to, a hexamethyldisilazane, a heptamethyldisilazane, etc. The alkali metal-containing material may include, but is not limited to, an n-butyllithium (nBu-Li), etc. The reaction between the aminosilane-based compound and the alkali metal-containing material may be performed in an organic solvent, for example, hexane, etc.

The aminosilane-based compound substituted with at least one alkali metal may be stoichiometrically reacted with a Te-containing compound substituted with halogen elements to obtain a Te precursor for lower temperature deposition having Te—N bonds and N—Si bonds. The Te-containing compound substituted with halogen elements may include, but is not limited to, a dichlorotellurium ($TeCl_2$), a difluorotellurium ($TeF_2$), etc. The reaction may be performed in a solvent, for example, THF, etc. The Te precursor according to example embodiments of the present invention obtained therefrom may be separated by various conventional purification and/or separation methods, and may be used as a deposition source for forming a thin layer.

A method of preparing a Te precursor according to example embodiments of the present invention was described above, however, the method is not limited to the above example embodiment and various variants thereof may be made.

Example embodiments of the present invention provide a Te-containing chalcogenide thin layer prepared by employing a Te precursor for lower temperature deposition containing Te, a 15-group compound (for example, N) and/or a 14-group compound (for example, Si). The chalcogenide thin layer may include As—Se—Te, As—Ti—Te, Ti—Se—As—Te, As—Ge—Te, Ge—Sb—Te, etc.

In other example embodiments, the chalcogenide thin layer may include other chalcogenide alloys such as germanium-antimony-tellurium (Ge—Sb—Te), arsenic-antimony-tellurium (As—Sb—Te), tin-antimony-tellurium (Sn—Sb—Te), or tin-indium-antimony-tellurium (Sn—In—Sb—Te), arsenic-germanium-antimony-tellurium (As—Ge—Sb—Te). Alternatively, the chalcogenide thin layer may include an element in Group VA-antimony-tellurium such as tantalum-antimony-tellurium (Ta—Sb—Te), niobium-antimony-tellurium (Nb—Sb—Te) or vanadium-antimony-tellurium (V—Sb—Te). Further, the chalcogenide thin layer may include an element in Group VIA-antimony-tellurium such as tungsten-antimony-tellurium (W—Sb—Te), molybdenum-antimony-tellurium (Mo—Sb—Te), or chrome-antimony-tellurium (Cr—Sb—Te).

Although the chalcogenide thin layer is described above as being formed primarily of ternary phase-change chalcogenide alloys, the chalcogenide alloy could be selected from a binary phase-change chalcogenide alloy or a quaternary phase-change chalcogenide alloy. Example binary phase-change chalcogenide alloys may include one or more of $Sb_2$—$Te_3$ or Ge—Te alloys; example quaternary phase-change chalcogenide alloys may include one or more of an Ag—In—Sb—Te, (Ge—Sn)—Sb—Te, Ge—Sb—(Se—Te) or $Te_{81}$—$Ge_{15}$—$Sb_2$—$S_2$ alloy, for example.

In an example embodiment, the chalcogenide thin layer may be made of a transition metal oxide having multiple resistance states, as described above. For example, the chalcogenide thin layer may be made of GST ($Ge_2Sb_2Te_5$).

Among those, example embodiments of the present invention also provide a thin layer made of Ge—Sb—Te (GST), prepared by employing a Ge precursor, a Sb precursor and a Te precursor for lower temperature deposition as set forth above.

The term "Te-containing chalcogenide thin layer doped with a 15-group compound (for example, N) and/or a 14-group compound (for example, Si)" or "GST thin layer doped with a 15-group compound (for example, N) and/or a 14-group compound (for example, Si)," or "GST phase-change thin layer doped with a 15-group compound (for example, N) and/or a 14-group compound (for example, Si)" refers herein to a Te-containing chalcogenide thin layer doped with a 15-group compound (for example, N) and/or a 14-group compound (for example, Si), or a thin layer made of Ge—Sb—Te-based material, or a phase-change thin layer doped with a 15-group compound (for example, N) and/or a 14-group compound (for example, Si).

The description of the Te precursor for lower temperature deposition may be as described above.

The Ge precursor and Sb precursor include, but are not limited to, any material that can be employed together with the Te precursor for lower temperature deposition, and may be optionally selected from known Ge precursors and Sb precursors. Such a Ge precursor may include, but is not limited to, $Ge(CH_3)_4$ or $Ge[N(CH_3)_2]_4$, etc. The Sb precursor may include, but is not limited to, $Sb(CH_3)_3$ or $Sb[N(CH_3)_2]_3$, etc. The composition ratio between Ge, Sb and Te in the GST thin layer doped with a 15-group compound (for example, N) and/or a 14-group compound (for example, Si) may vary. Among these, a GST thin layer doped with a 15-group compound (for example, N) and/or a 14-group compound (for example, Si) according to example embodiments of the present invention may be, made of, for example, $Ge_2Sb_2Te_5$ material doped with a 15-group compound (for example, N) and/or a 14-group compound (for example, Si).

Figure 3:
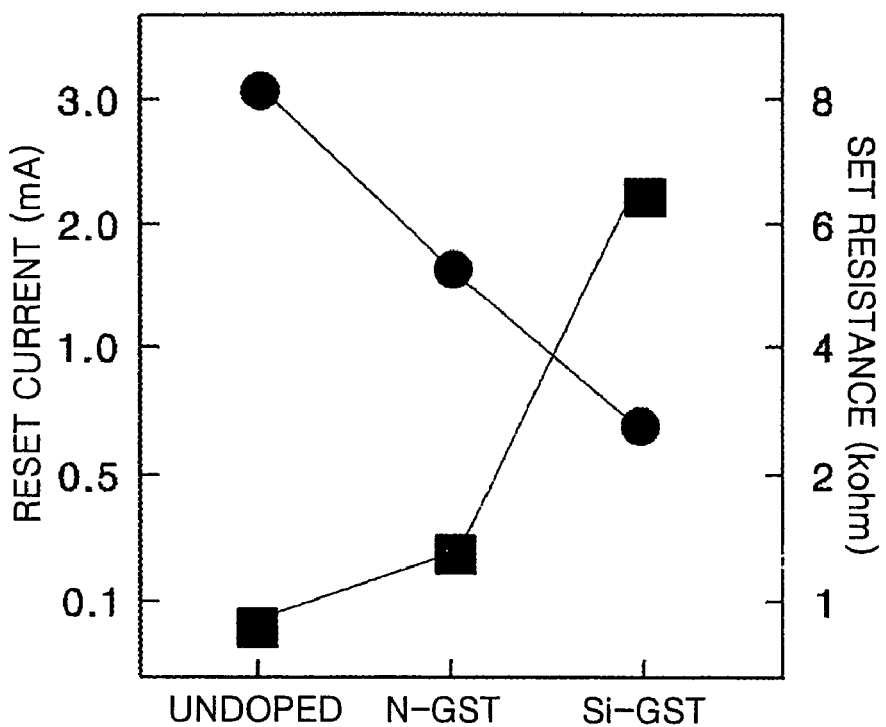
FIG. 3 is a graph showing the reset current (mA) and set resistance value (kΩ) of example materials constituting a phase change layer.

A thin layer doped with a 15-group compound (for example, N) and/or a 14-group compound (for example, Si) may perform a phase-change from a crystalline state to an amorphous state using a smaller reset current. Further, the thin layer may have an increased set resistance. FIG. 3 is a graph showing the reset current (mA) and set resistance value according to the material constituting a phase change thin layer. To measure the reset current and set resistance value, TiN was used as an upper electrode and a lower electrode, and a phase-change layer GST ($Ge_2Sb_2Te_5$) layer, a GST layer doped with a 15-group compound (for example, N) and a GST layer doped with a 14-group compound (for example, Si) were used between both electrodes, respectively, to form the PRAMs. The electric current value, where the phase-change layer state can be changed from a crystalline state to an amorphous state, e.g., reset current value and set resistance value were measured.

Referring to FIG. 3, for a GST that is not doped with impurities, the reset current value is higher, e.g., 3 mA and the set resistance value is lower, e.g., about 0.8 kΩ. For the GST doped with a 15-group compound (for example, N), 1.5 mA of reset current is needed and the set resistance value is about 1.5 kΩ. Further, when the GST doped with a 14-group compound (for example, Si) is formed as a phase-change layer, a lower value, e.g., about 0.7 mA of the reset current is needed, and the set resistance value is a higher value, e.g., 6.2 kΩ. Consequently, when a 15-group compound (for example, N) and/or a 14-group compound (for example, Si) is doped, the reset current value is decreased and/or the set resistance value is increased, while the phase-change characteristics of the GST phase-change layer are maintained. Si and/or N, included in the GST phase-change layer as an impurity, may facilitate the phase change from a crystalline state to an amorphous state at lower temperatures.

A method of preparing a thin layer, for example, a Te-containing chalcogenide thin layer, doped with a 15-group compound (for example, N) and/or a 14-group compound (for example, Si) according to example embodiments of the present invention may include depositing the Te precursor described above at deposition temperatures below 350° C. The Te-containing chalcogenide thin layer may be various known chalcogenide thin layer, and among these, may be a Ge—Sb—Te (GST) thin layer prepared by employing a Ge precursor, a Sb precursor and the Te precursor at a deposition temperature of about 350° C. or less. The description of the Ge precursor, the Sb precursor and the Te precursor may be as described above.

According to a method of preparing a thin layer, for example, a Te-containing chalcogenide thin layer, doped with a 15-group compound (for example, N) and/or a 14-group compound (for example, Si), the deposition temperatures may be lower than that used in the preparation method employing a conventional precursor can be employed. For example, the deposition temperatures in the method of preparing the thin layer doped with a 15-group compound (for example, N) and/or a 14-group compound (for example, Si) according to example embodiments of the present invention may be below about 350° C. The lower limit of the deposition temperatures may vary according to the thickness of the thin layer to be formed and/or the cation ratio, for example the Te/(Ge+Sb) cation ratio. For example, when a GST thin layer doped with a 15-group compound (for example, N) and/or a 14-group compound (for example, Si) with a thickness of 330 Å is formed, the lower limit of the deposition temperatures may be about 200° C. In a method of forming a Te-containing chalcogenide thin layer doped with a 15-group compound (for example, N) and/or a 14-group compound (for example, Si) according to example embodiments of the present invention, the deposition temperatures may be below about 350° C., for example, 200° C. to 350° C., for example, 250° C.

Such deposition temperatures are distinguished from those of a deposition process employing a conventional precursor. When a chalcogenide thin layer is formed by employing a conventional precursor, it is known that a deposition temperature of greater than about 500° C. is needed to prepare a thin layer having a desired thickness suitable for various devices. However, a component, for example Te, of the precursor exposed to temperatures higher than about 350° C. may evaporate. As a result, a chalcogenide thin layer having a desired cation ratio may be difficult to form.

However, when a precursor for lower temperature deposition according to example embodiments of the present invention is deposited at lower temperatures, for example, below about 350° C., a thin layer having a more uniform thickness suitable for various devices may be formed. For example, when the Te precursor is deposited together with a Ge precursor and a Sb precursor, a GST thin layer having a more uniform thickness suitable for various devices may be formed. Also, a thin layer having a desired Te/(Ge+Sb) cation ratio may be effectively formed without loss of raw material because the Te components are less likely to evaporate. Further, if a Te precursor for lower temperature deposition containing a 15-group compound (for example, N) and/or a 14-group compound (for example, Si) as deposition source is used, it is not necessary to separately dope with a 15-group compound (for example, N) and a 14-group compound (for example, Si) to obtain a Te-containing chalcogenide doped with a 15-group compound (for example, N) and a 14-group compound (for example, Si).

The method of preparing a Te-containing chalcogenide thin layer doped with a 15-group compound (for example, N) and/or a 14-group compound (for example, Si) according to example embodiments of the present invention may employ a deposition method, for example, a chemical vapor deposition (CVD) or an atomic layer deposition (ALD), but the deposition methods are not limited to these examples. The CVD and ALD may be known techniques. Plasma enhanced chemical vapor deposition (PECVD) or plasma enhanced atomic layer deposition (PEALD) employing plasma may be also employed. The PECVD or PEALD may employ, for example, $H_2$ and/or $NH_3$ plasma sources. Examples of CVD and ALD may be found, for example, in U.S. Patent Application No. 2003/0185981 to Min et al., published on Oct. 2, 2003, U.S. Pat. No. 6,752,869 to Lee et al., issued on Jun. 22, 2004, and Korean Patent Laid-Open Publication No. 2002-0084616, the disclosures of which are herein incorporated by reference, in their entirely.

A thin layer doped with a 15-group compound (for example, N) and/or a 14-group compound (for example, Si) formed by employing a precursor for lower temperature deposition according to example embodiments of the present invention may have the characteristics of a phase-change layer. By employing such characteristics, the thin layer may be applied, for example, as a phase-change layer in a phase-change memory device. Hereinafter, a phase-change memory device including a phase-change layer formed by employing a Te precursor for lower temperature deposition and the method of preparing the same will be described.

Figure 4:
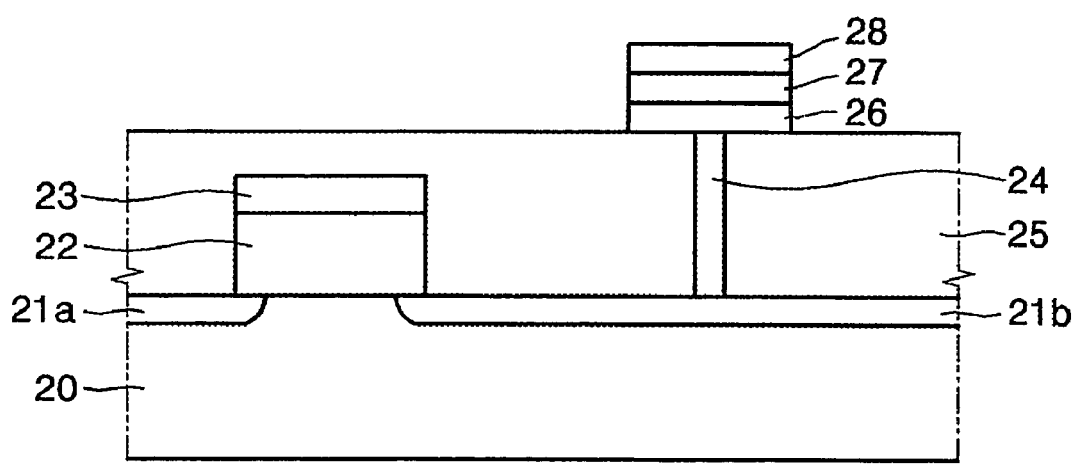
FIG. 4 is a schematic cross-sectional view of a phase-change memory device including a thin layer, for example a GST thin layer, doped with a 15-group compound and/or a 14-group compound according to an example embodiment of the present invention.

FIG. 4 is a cross-sectional view of a phase-change memory device prepared according to example embodiments of the present invention.

Referring to FIG. 4, on a transistor substrate 20 doped with n type or p type, a first impurity area 21a and a second impurity area 21b may be formed such that both areas may have a polarity opposite to that of the transistor substrate 20. An area of the transistor substrate 20 between the first impurity area 21a and the second impurity area 21b may be referred to as a channel area, and on the channel area, a gate insulating layer 22 and a gate electrode layer 23 may be formed.

On the first impurity area 21a, the gate electrode layer 23 and the second impurity area 21b, the insulating layer 25 may be formed, and a contact hole exposing the second impurity area may be formed in the insulating layer 25. In the contact hole, a conductive plug 24 may be formed, and on the conductive plug 24, the lower electrode 26, the phase-change layer 27 and the upper electrode 28 may be sequentially formed. The phase-change memory device according to example embodiments of the present invention may be a GST thin layer (or any of the chalcogenide materials described above) in which the phase-change layer 27 contains Si and/or N as described above. For example, the GST material may be $Ge_2Sb_2Te_5$.

The transistor structure under the phase-change layer 27 may be formed by a conventional transistor preparing process. In the structure of FIG. 4, the lower electrode 26 and the conductive plug 24 may be integrally formed. For example, the phase-change layer 27 may be formed on the conductive plug 24 such that the conductive plug acts directly as the lower electrode 26, and electric current can be directly applied to the phase-change layer 27 to induce generation of Joule heat. In an example embodiment, the conductive plug 24 may be used as a heating plug.

A process of preparing a phase-change memory device according to example embodiments of the present invention may be as follows. On the transistor substrate 20, materials to form the gate insulating layer 22 and the gate electrode layer 23 may be applied sequentially. Both sides of the material to form the gate insulating layer 22 and the gate electrode layer 23 may be removed to form the gate insulating layer 22 and the gate electrode layer 23. On a surface of the transistor substrate 20 above both sides of the exposed gate insulating layer 22 and the gate electrode layer 23, impurities may be applied to form the first impurity area 21*a* and the second impurity area 21*b*. On the first impurity area 21*a*, the gate electrode layer 23 and the second impurity area 21*b*, the insulating layer 25 may be formed. The contact hole may be formed on the insulating layer 25 such that the second impurity area 21*a* is exposed, and the contact hole may be filled with conductive material to form the conductive plug 24.

Optionally, a noble metal material that is a conductive material, or a metal nitride, for example, TiN, etc. may be applied on the conductive plug 24 to form the lower electrode 26. Conventionally, a sputtering process was used to form the phase-change layer 27 on the conductive plug 24 or the lower electrode 26.

However, in example embodiments of the present invention, a GST phase-change layer containing a 15-group compound (for example, N) and/or a 14-group compound (for example, Si) may be formed by reacting the Te precursor for lower temperature deposition containing Te, a 15-group compound (for example, N) and/or a 14-group compound (for example, Si) with a Ge precursor and a Sb precursor on the substrate within a reaction chamber. The deposition temperature may be, for example, below 350° C., for example, 200° C. to 350° C. A phase-change memory device according to example embodiments of the present invention may be completed by applying a conductive material on the phase-change layer 27 as in the lower electrode 26 to form the upper electrode 28.

The present invention will be described in greater detail with reference to the following examples. The following examples are for illustrative purposes and are not intended to limit the scope of the invention.

EXAMPLES

Example 1

Reaction scheme I

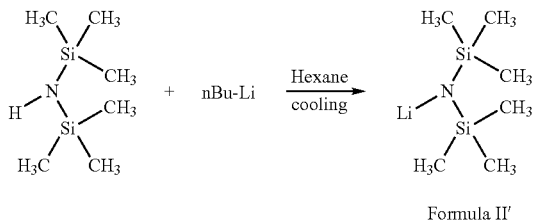

Formula II'

As in the reaction scheme I, 0.1 mole of hexamethyldisilazane solution and 0.2 mole of nBu-Li were mixed in 1000 ml of hexane at −78° C. and ambient pressure, and then the mixture was reacted for 4 hours at room temperature to obtain the compound represented by formula II' above.

Reaction scheme II

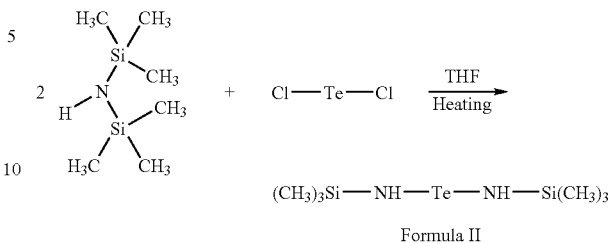

$(CH_3)_3Si-NH-Te-NH-Si(CH_3)_3$

Formula II

Figure 5A:
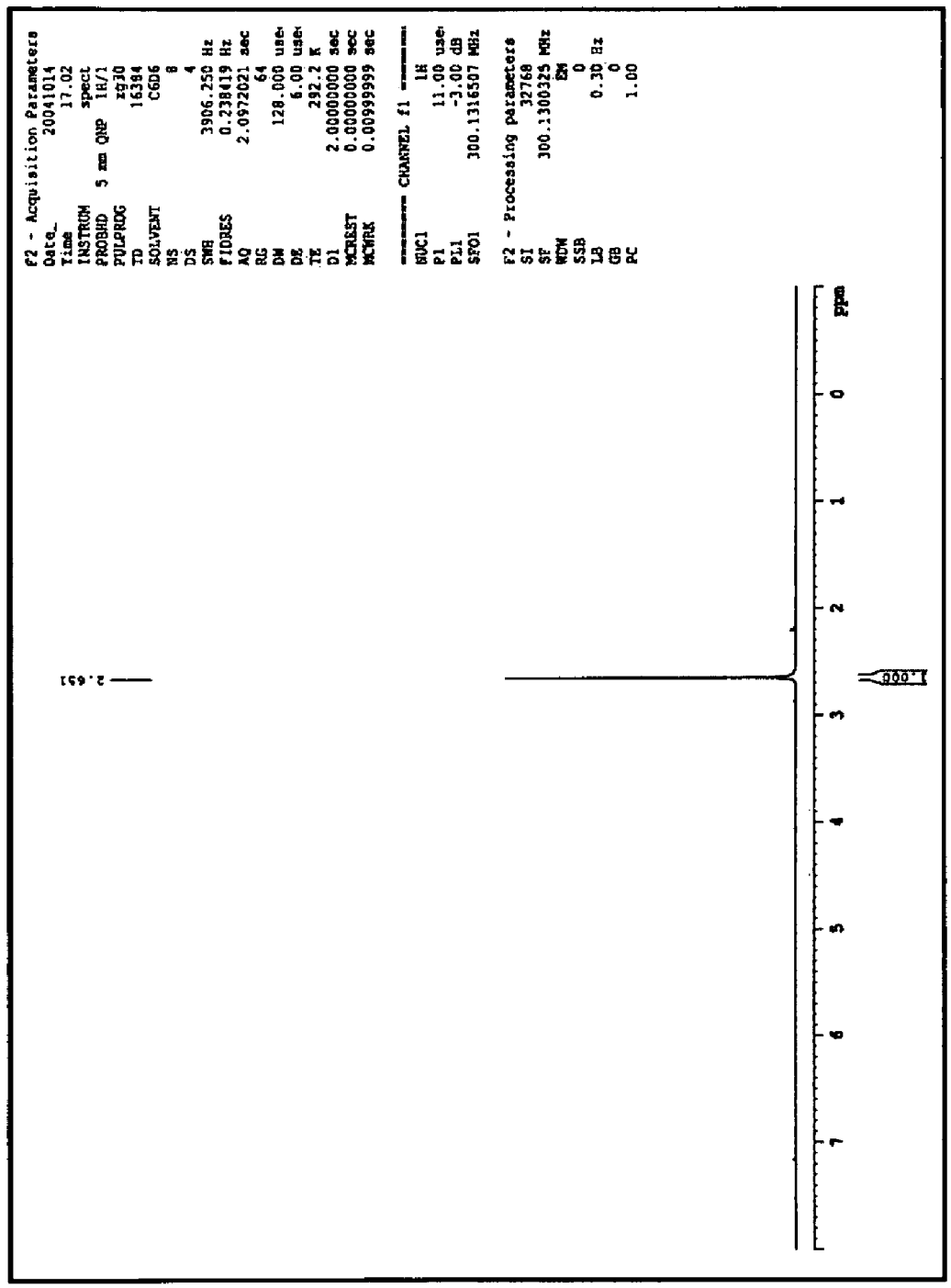
FIGS. 5A and 5B show the results of 1H-NMR analysis and 13C-NMR analysis for a Te precursor for lower temperature deposition according to an example embodiment of the present invention, respectively.
Figure 5B:
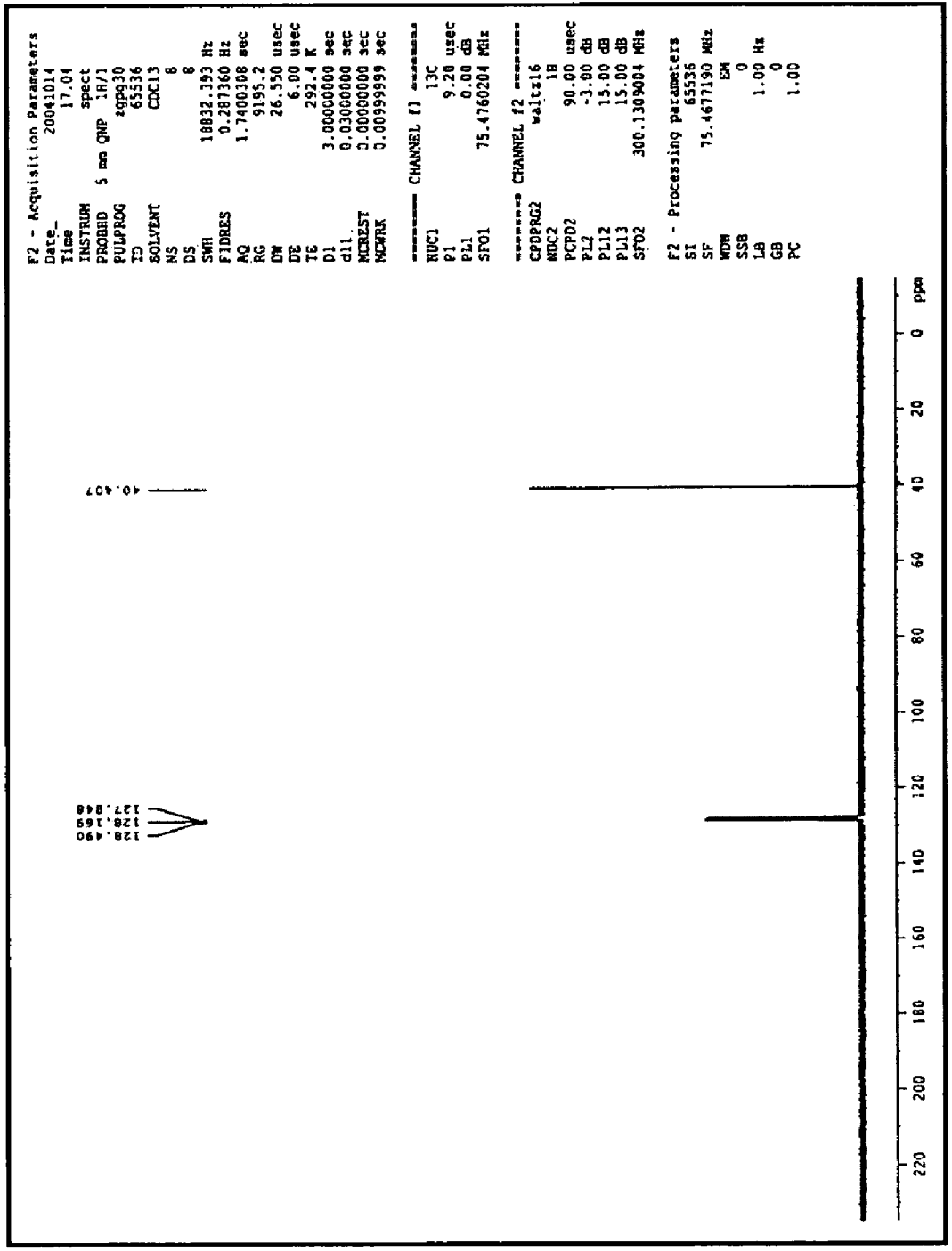

As in the reaction scheme II, 0.5 mole of the compound represented by the formula II' and 0.5 mole of TeCl2 were mixed in 1000 ml of THF, and then the mixture was heated for 8 hours at 150° C. The mixture was evaporated at ambient temperature in a vacuum, fractional distillation was performed for synthesized Te precursor at 0.1 torr and 60° C. to obtain 24 g of the compound represented by formula II, e.g., $Te[NH(Si(CH_3)_3)]_2$, and then 1H-NMR analysis and 13C-NMR analysis (all analysis was performed at C6D6 and 25° C.) were performed and the results are shown in FIGS. 5A and 5B, respectively. From FIGS. 5A and 5B, Te—N bond and N—Si bond of the compound of the formula II can be confirmed. The compound of the formula II refers to a Te precursor 1.

Evaluation Example 1

Figure 6:
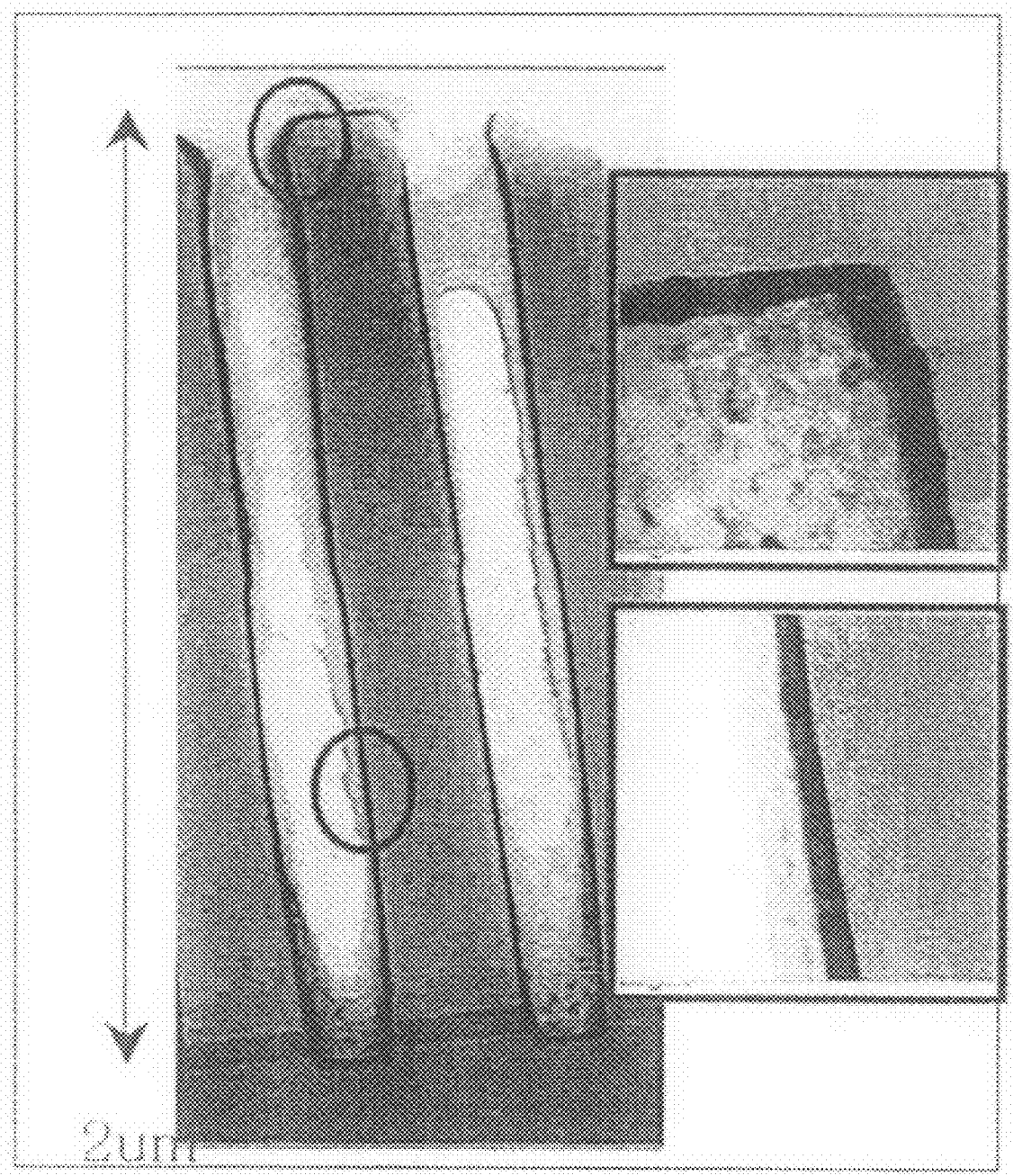
FIG. 6 is a SEM photograph of a pattern obtained by depositing the Te precursor according to an example embodiment of the present invention at 250° C.

The Evaluation of the Performance for Patterning of the Te Precursor 1 at a Lower Deposition Temperature The performance for patterning by ALD process was evaluated by employing the Te precursor 1, and the results are shown in FIG. 6. The Si substrate including a plurality of concave parts having a depth of 18000 Å and a width of 960 Å was prepared as the substrate, on which the Te precursor 1 is deposited to form a layer, and the detailed deposition conditions were as set forth in Table I below.

TABLE 1

| Deposition temperature | 250° C. |
|---|---|
| Deposition cycle | 250 times |
| Process time | 0.006/3/1/1 |
| Ar influx | 500 sccm |
| H₂ influx | 300 sccm |
| Plasma power | 100 W |

Referring to FIG. 6, it can be seen that the deposition products of the Te precursor 1 are evenly packed throughout the concave part having a pattern to follow the white line. From this result, it can be seen that the Te precursor 1 according to example embodiments of the present invention has improved patterning performance.

Preparation Example

Formation of a Layer Made of a GST Material and its Resistance Evaluation

Figure 7:
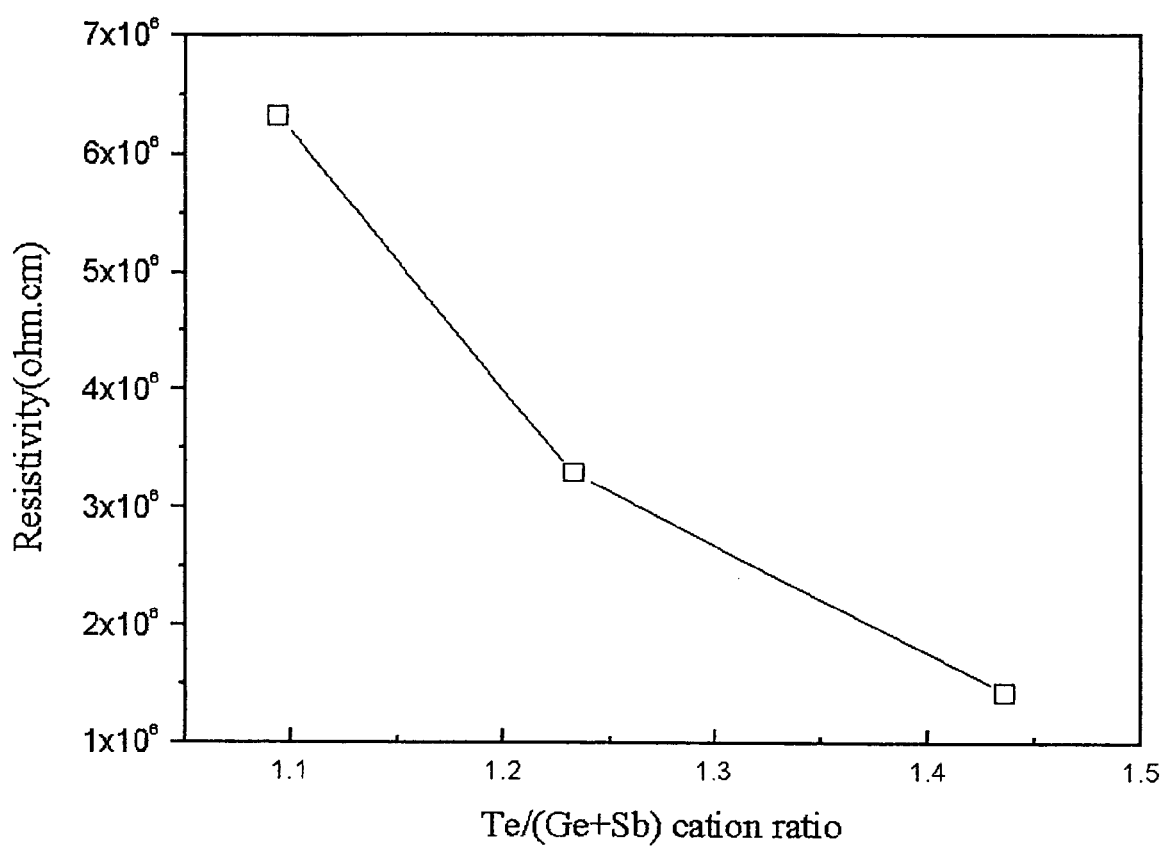
FIG. 7 is a graph illustrating the resistance of a thin layer, for example, a GST thin layer, doped with a 15-group compound (for example, N) and a 14-group compound (for example, Si) obtained by depositing a Ge precursor, a Sb precursor, and a Te precursor according to an example embodiment of the present invention to obtain a desired Te/(Ge+Sb) cation ratio.

A $Ge_2Sb_2Te_5$ layer doped with a 15-group compound (for example, N) and/or a 14-group compound (for example, Si) through the ALD process was formed by employing $Ge[N(CH_3)_2]_4$ as a Ge precursor, $Sb[N(Si(CH_3)_3)_3]$ as a Sb precursor, and the Te precursor 1 as a Te precursor. The detailed conditions of the ALD process is the same as described in Table 1. Further, the Te/(Ge+Sb) cation ratio was controlled to be about 1.1, 1.25, and 1.45. The resistance of the GST thin layer doped with a 15-group compound (for example, N) and/or a 14-group compound (for example, Si) obtained above was measured, and the results are shown in FIG. 7. According to FIG. 7, it can be seen that the resistance of the GST thin layer doped with a 15-group compound (for example, N) and/or a 14-group compound (for example, Si) decreases as Te/(Ge+Sb) cation ratio increases, that is, temperature increases.

The Te precursor for lower temperature deposition according to example embodiments of the present invention may be deposited at lower temperatures for forming a Te-containing thin layer, for example, a Te-containing chalcogenide thin layer doped with a 15-group compound (for example, N) and/or a 14-group compound (for example, Si), for example, a GST thin layer. The GST phase-change layer doped with a 15-group compound (for example, N) and/or a 14-group compound (for example, Si) formed by employing a Te precursor for lower temperature deposition may have a lower reset current, and thus when a memory device including the same is employed, its integration may be possible, and operation with higher capacity and/or higher speed may be possible.

While the present invention has been particularly shown and described with reference to example embodiments thereof, it will be understood by those of ordinary skill in the art that various changes in form and details may be made therein without departing from the spirit and scope of the present invention as defined by the following claims.

What is claimed is:

1. A Te precursor represented by formula II below:

$$Te[NH(Si(CH_3)_3)]_2 \qquad \text{II}$$

* * * * *